United States Patent
Jol et al.

(10) Patent No.: US 10,591,430 B2
(45) Date of Patent: Mar. 17, 2020

(54) METHOD AND SYSTEM FOR DETECTING MOISTURE ON A CONNECTOR CONTACT

(71) Applicant: Apple Inc., Cupertino, CA (US)

(72) Inventors: Eric S. Jol, San Jose, CA (US); Jason S. Sloey, Cedar Park, TX (US); Craig C. Birrell, Sunnyvale, CA (US); Samuel B. Schaevitz, Los Gatos, CA (US); Ching Yu John Tam, Los Gatos, CA (US); Nagendra Bage Jayaraj, San Jose, CA (US)

(73) Assignee: Apple Inc., Cupertino, CA (US)

( * ) Notice: Subject to any disclaimer, the term of this patent is extended or adjusted under 35 U.S.C. 154(b) by 260 days.

(21) Appl. No.: 15/699,987

(22) Filed: Sep. 8, 2017

(65) Prior Publication Data

US 2019/0079037 A1 Mar. 14, 2019

(51) Int. Cl.
*G01N 27/04* (2006.01)
*G01R 31/04* (2006.01)
*H01R 13/66* (2006.01)
*G01M 3/16* (2006.01)

(52) U.S. Cl.
CPC .......... *G01N 27/048* (2013.01); *G01R 31/04* (2013.01); *H01R 13/6683* (2013.01); *G01M 3/16* (2013.01)

(58) Field of Classification Search
CPC .............................. G01R 31/04; G01N 27/048
USPC .......... 324/500, 538, 514, 756.05, 600, 694, 324/754.04–754.15, 452–453, 200, 204
See application file for complete search history.

(56) References Cited

U.S. PATENT DOCUMENTS

| | | |
|---|---|---|
| 3,927,351 A | 12/1975 | Lambertsen |
| 6,313,646 B1 | 11/2001 | Davis et al. |
| 6,318,172 B1 | 11/2001 | Byatt et al. |
| 6,885,201 B2 | 4/2005 | Germiquet et al. |
| 7,571,637 B2 | 8/2009 | Chen et al. |
| 9,335,355 B2 | 5/2016 | Menzel et al. |
| 2006/0058069 A1 | 3/2006 | Garcia et al. |
| 2006/0208914 A1 | 9/2006 | Liu et al. |
| 2012/0299555 A1 | 11/2012 | Tam et al. |

(Continued)

FOREIGN PATENT DOCUMENTS

| | | |
|---|---|---|
| CN | 104067184 A | 9/2014 |
| CN | 106598818 A | 4/2017 |

(Continued)

OTHER PUBLICATIONS

International Search Report and Written Opinion for PCT/US2018/048253 dated Dec. 12, 2018, 15 pages.
Office Action for TW107130420 dated Dec. 17, 2019, 12 pages.

*Primary Examiner* — Melissa J Koval
*Assistant Examiner* — Trung Nguyen
(74) *Attorney, Agent, or Firm* — Kilpatrick Townsend & Stockton LLP

(57) ABSTRACT

An electronic device comprising a connector including a plurality of contacts and a liquid detection module coupled to at least one contact in the plurality of contacts. The liquid detection module can be configured to generate and apply a time varying voltage or current to the at least one contact over a range of frequencies, measure complex impedance including phase and magnitude at the at least one contact, and determine whether liquid intrusion has occurred on the contacts based on previously measured signatures of phase and magnitude versus frequency.

20 Claims, 7 Drawing Sheets

(56) References Cited

U.S. PATENT DOCUMENTS

2014/0313039 A1\* 10/2014 Stevens ................. H03K 17/94
                                                              340/604
2016/0313270 A1    10/2016 Connell et al.
2017/0110835 A1\*  4/2017 Hasegawa .......... H01R 13/6683
2017/0358922 A1   12/2017 Bacon et al.

FOREIGN PATENT DOCUMENTS

| EP | 2390673 A2 | 11/2011 |
| EP | 2680043 | 1/2014 |
| TW | 201301625 A1 | 1/2013 |
| WO | 2013/007542 | 1/2013 |

\* cited by examiner

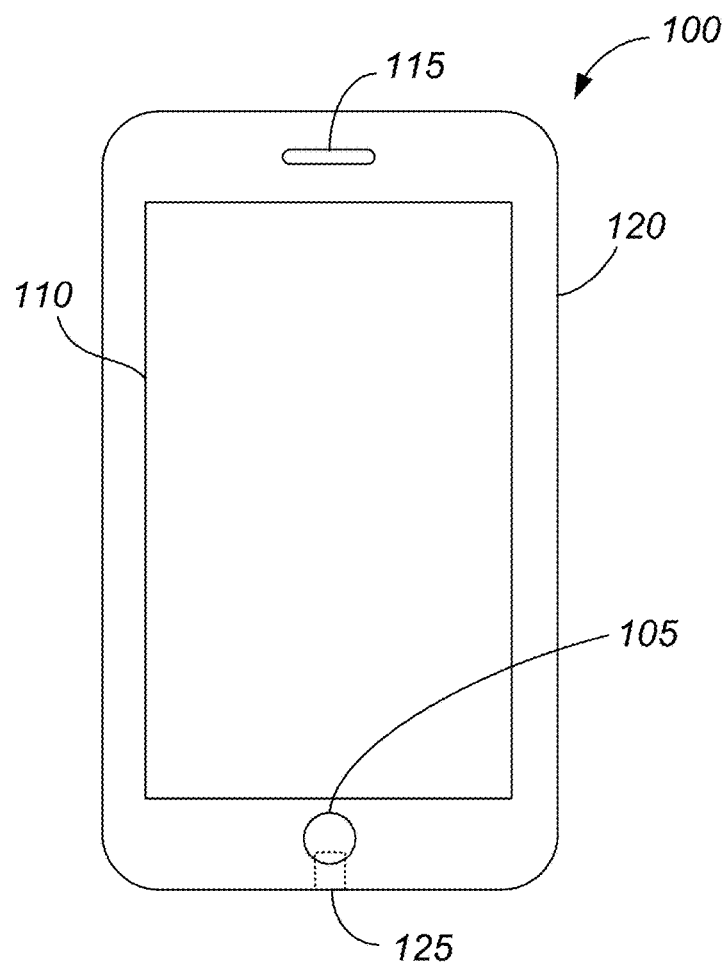
FIG. 1
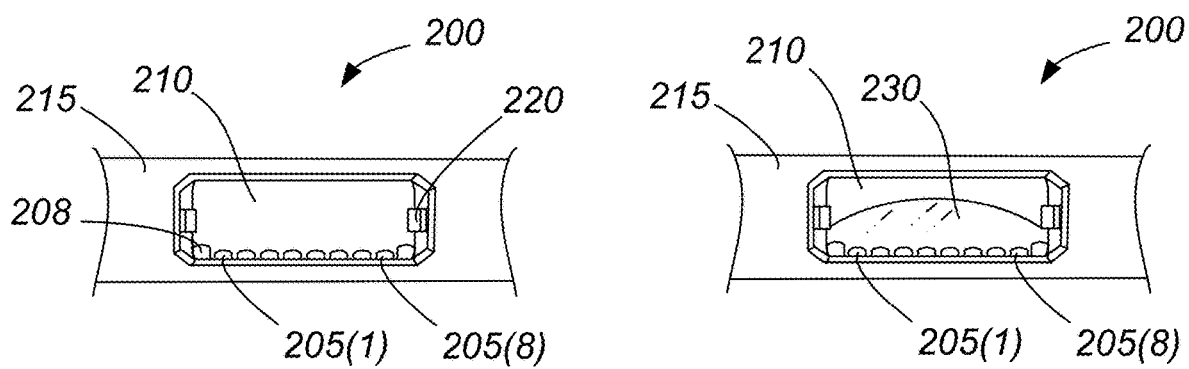
FIG. 2A
FIG. 2B

| Likely to be Dry | Likely to be Liquid |
|---|---|
| Impedence > 300 kohms | Impedance falling 10 Hz to 1 kHz |
| Impedance flat from 10 Hz to 1 kHz | Phase < -30 at 10 Hz |
| Phase = 0 at 100 Hz | Phase < -10 at 10 Hz and 1 kHz |
| Phase at 10 kHz matches characteristics <100pF | |

METHOD AND SYSTEM FOR DETECTING MOISTURE ON A CONNECTOR CONTACT

FIELD

Embodiments of the disclosure relate generally to techniques and systems for detecting the presence of a liquid, such as water, on one or more contacts of an external connector of a portable electronic device.

BACKGROUND

Portable electronic devices, such as smartphones and tablet computers, can be exposed to liquid or moisture during their normal use. For example, such devices may be exposed to rain, or sweat or an accidental liquid spill. Additionally, in some instances the devices may be waterproof or highly water resistant in which case a user may knowingly expose the device to water when swimming or to wash the device.

Many portable electronic devices include a receptacle connector that has an opening or port at an exterior of the device in which multiple contacts reside. A corresponding plug connector can be inserted into the receptacle connector port to charge the internal battery of the device, to transfer data between the device and a second device, or for audio or video input or output, among other functions. If the contacts within the connector port are exposed to liquid while a voltage is applied to one or more of the contacts a short circuit could damage the connector or electronic device. Additionally, ions and other solids or materials within the liquid can react with the electrical contacts causing corrosion and other damage.

Some electronic devices include a liquid contact sensing circuit within the device that takes measurements, such as resistance and capacitance measurements, across one or more of the electrical contacts of the device in order to detect the presence of liquid on those contacts. In response to detecting the presence of liquid corrective actions can be taken in real time. For example, the electronic device can power down certain sensitive electronic components within the device. Alternatively, or additionally, the electronic device can reduce or terminate power supplied to its connector such that the voltage across electrical contacts of the connector is reduced or dropped to zero in response to having detected the presence of short-circuit or corrosion causing moisture within the port.

While terminating or reducing power supplied to a connector can prevent damage to the electronic device and/or connector, it can also cause user frustration if the liquid sensing circuit incorrectly determines that a harmful liquid is present on the contacts. For example, not all liquid is likely to result in contact corrosion. Some liquids that have minimal or no dissolved materials within them are not a serious concern for likely contact corrosion. Similarly, the liquid sensing circuit might incorrectly determine that solid material (e.g., dirt, dust, grease, etc.) that is present on one or more of the contacts is a harmful liquid and act accordingly even though the solid material does not present a safety or corrosion concern.

Thus, despite the existence of various known liquid detection methods and circuits, new and improved methods for detecting liquid at a connector of a portable electronic device and distinguishing potentially harmful liquids from other contaminants are desirable.

BRIEF SUMMARY

Embodiments of the disclosure pertain to a system and method for reliably detecting the presence of a short circuit-causing liquid (e.g. sweat, pool water, tap water, sea water, rain, or a beverage) in an external connector of an electronic device, such as a portable consumer electronics device. Embodiments can also protect the electronic device from potential damage and/or corrosion on contacts of the external connector that may otherwise occur by continued presence of the liquid on powered contacts of the connector. Embodiments of the disclosure can provide such protection while distinguishing instances when solids or liquids that are not likely to be harmful are present on one or more contacts instead of potentially harmful liquids being present at the connector contacts.

If a liquid is present on a connector contact, ions of opposing polarity can form at the boundary between the contact and liquid when a voltage is applied to the contact. Typically, a single layer of liquid molecules adheres to the surface of the contact and forms between the two layers of opposing polarity ions separating the two layers and acting like a dielectric in capacitor. This phenomenon is sometimes referred to as the double layer capacitance effect. Some embodiments of the disclosure apply a time varying voltage to a connector contact (e.g., a sinusoidal wave) at multiple frequencies and monitor reactance (both magnitude and phase) at the contacts to determine if an harmful liquid is present on a contact. If a liquid is present on the contact, the contact will be highly capacitive which will impact the signals phase change. The liquid coated contact will also exhibit significant frequency dependence being more highly conductive at higher frequencies and less conductive at lower frequencies.

In some embodiments an electronic device is provided that includes a connector having a plurality of contacts and a liquid detection module coupled to at least one contact in the plurality of contacts. The liquid detection module can be configured to generate and apply a time varying voltage or current to the at least one contact over a range of frequencies, measure complex impedance including phase and magnitude at the at least one contact, and determine whether liquid intrusion has occurred on the contacts based on previously measured signatures of phase and magnitude versus frequency.

In some embodiments the electronic device may further include communication circuitry that enables the electronic device to communicate with another electronic device over the at least one contact and a multiplexor is configured to switch the at least one contact between the communication circuitry and the liquid detection circuitry. The liquid detection module can generate the time varying voltage or current as a sinewave from a pulse density modulation (PDM) signal and can convert the current sinewave to a voltage sinewave that is applied to the at least one contact in the plurality of contacts. In various examples the liquid detection module can include a low pass filter that receives a PDM signal as input and outputs a current sinewave, a transimpedance amplifier that receives a current sinewave as input and generates a voltage sinewave as output, and/or an audio codec that processes received signals to determine whether liquid intrusion has occurred on the contacts based on previously measured signatures of phase and magnitude versus frequency.

In some embodiments the liquid detection module can employ a test that includes detecting whether the measured impedance on the at least one contact is greater than a predetermined amount and whether the measured phase on the at least one contact is essentially zero at a predetermined frequency to determine whether liquid intrusion has occurred on the contacts based on previously measured signatures of phase and magnitude versus frequency.

In some embodiments an electronic device according to the disclosure can include: a connector comprising a plurality of contacts including at least a voltage contact and a signal contact; signal generating circuitry configured to generate a control signal or data signal; a digital processor configured to generate a pulse density modulation (PDM) signal, receive complex impedance measurements of the at least one contact including phase and magnitude from the analog-to-digital converter, and determine whether liquid intrusion has occurred on one or more of the contacts based on previously measured signatures of phase and magnitude versus frequency; a low pass filter configured to receive the pulse density modulation (PDM) signal at an input and output a current sine wave at a frequency indicated by the PDM signal; a transimpedance amplifier coupled at an input to receive the current sinewave from the low pass filter and output a voltage sine wave; an analog-to-digital converter having a first input coupled to the output of the low pass filter and a second input coupled to the output of the transimpedance amplifier; and a multiplexor coupled to the signal generating circuitry, to the output of the transimpedance amplifier and to the signal contact, the multiplexor configured to switch the signal contact between the signal generating circuitry and the transimpedance amplifier.

In some embodiments a method of detecting a liquid on a contact of a connector is provided. The method can include: generating and apply a time varying voltage or current to the contact over a range of frequencies; measuring complex impedance including phase and magnitude at the contact; and determining whether liquid intrusion has occurred on the contacts based on previously measured signatures of phase and magnitude versus frequency. The step of generating and applying can include generating a current sine wave from a pulse density modulation (PDM) signal and converting the current sinewave to a voltage sinewave that is applied to the contact. If it is determined that a liquid is present on the contact, the method can do one or more of the following: reduce the voltage on the contact, terminate the voltage on the contact or delay initiation of a function until a predetermined amount of time has expired. In some examples, the method can further include, prior to the generating and applying step, decoupling the contact from a first set of circuitry within an electronic device and coupling the contact to second set of circuitry to perform the generating and applying step.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the claims filed with the application.

BRIEF DESCRIPTION OF THE DRAWINGS

Embodiments of the disclosure are illustrated herein by way of example and not by way of limitation in the figures of the accompanying drawings in which like references indicate similar elements.

FIG. 1 shows a top view of an electronic media device in accordance with some embodiments of the disclosure;

FIG. 2A shows a front plan view of a receptacle connector that can be incorporated in electronic media device 100 shown in FIG. 1 according to some embodiments of the disclosure;

FIG. 2B shows a front plan view of receptacle connector 200 shown in FIG. 2A with a liquid present on the connector contacts;

DETAILED DESCRIPTION

Figure 3:
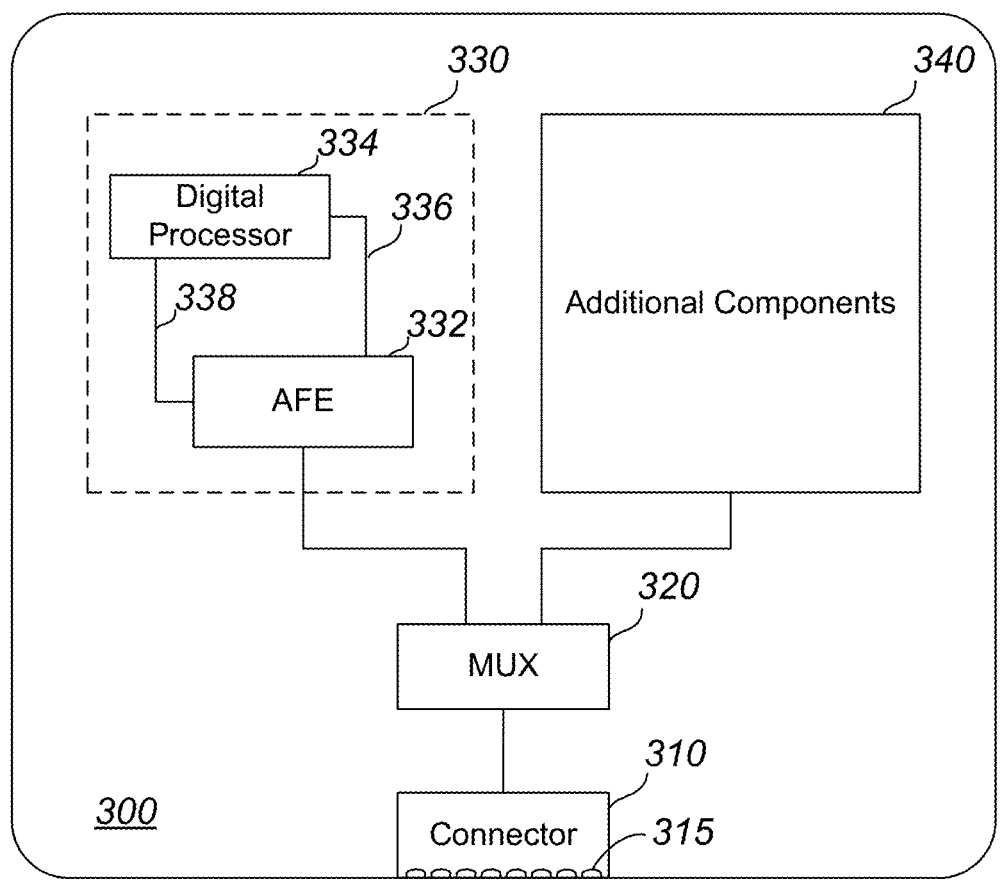
FIG. 3 is a simplified block diagram of circuitry within a portable electronic device 300 according to some embodiments of the disclosure.

Embodiments of the present disclosure will now be described in detail with reference to certain examples thereof as illustrated in the accompanying drawings. In the following description, numerous specific details are set forth in order to provide a thorough understanding of embodiments of the present disclosure. It will be apparent, however, to one skilled in the art, that embodiments of the present disclosure may be practiced without some or all of these specific details. In other instances, well known details have not been described in detail in order not to unnecessarily obscure embodiments of the present disclosure.

Some embodiments of the disclosure pertain to a system and method for reliably detecting the presence of a short circuit-causing liquid (e.g. sweat, pool water, tap water, sea water, rain, or a beverage) in an external connector of an electronic device, such as a consumer electronics portable device, and also for mitigating corrosion on the external connector that would be caused by continued presence of the liquid on powered contacts of the connector. An example of one type of portable consumer electronic device in which embodiments of the disclosure can be beneficially employed is shown in FIG. 1, which depicts a front view of one an electronic media device 100 that can be, for example, a smart phone. Among other elements, media device 100 can include a multipurpose button 105 as an input component, a touch screen display 110 as both an input and output component, and a speaker 115 as an output component, all of which are housed within a device housing 120.

Device 100 can also include a receptacle connector 125 having a cavity that opens to an exterior surface of housing 120. Electrical contacts (not shown in FIG. 1) can be positioned within the cavity, and a corresponding plug connector can be inserted into the cavity and mated with the receptacle connector such that electrical signals (e.g., data and power) can be transferred between device 100 and another electronic device through the mated connectors.

For simplicity, various internal components, such as the control circuitry, graphics circuitry, bus, memory, storage device and other components of electronic media device 100 are not shown in FIG. 1. Additionally, in some embodiments, electronic media device 100 can include more than one receptacle connector 125 and/or can include other types of receptacle connectors, such as a USB connector, an audio jack or other type of connector, that can benefit from the techniques of the present disclosure.

FIG. 2A is a front plan view of a receptacle connector 200 that can be representative of connector 125. Connector 200 enables an external device (e.g., an accessory device) having a mating connector (see e.g., connector 1100 shown in FIG. 11) to be physically coupled to the portable electronic device in which connector 200 is housed (e.g., device 100). Receptacle connector 200 includes eight contacts 205(1) . . . 205(8) that are spaced apart in a single row. The contacts are positioned within a cavity 210 that opens to an exterior surface 215 the electronic device (e.g., device 100).

Receptacle connector 200 can also include first and second retention mechanisms 220 on opposing sides of cavity 210 that engage with retention features of a corresponding plug connector to secure the plug connector within cavity 210 once the connectors are mated. Retention mechanisms 220 can be, for example springs, and can be made from an electrically conductive material to double as ground contacts. Receptacle connector can further include two contacts 225 (sometimes referred to as "connector detect" contacts) that are positioned slightly behind and on each side of the row of contacts 205(1) . . . 205(8). Contacts 225 can be used to detect when the plug connector 240 is inserted within cavity 210 as well as when the plug connector 240 is pulled out of cavity 210 and disengaged from connector 200.

Since cavity 210 is exposed at exterior surface 215 of an electronic device, it is possible for a liquid (e.g., water or sweat) to get into the cavity and cover one or more of contacts 205(1) . . . 205(8). For example, as shown in FIG. 2B a liquid 230 has collected within cavity 210 and covers all of the contacts 205(1) . . . 205(8). As described below, embodiments of the disclosure can detect the presence of liquid 230 by applying a time-varying voltage to one of the individual contacts at different frequencies and measuring the complex impedance.

Some embodiments of the disclosure pertain to a system and method for protecting an electronic device, such as a consumer electronics portable device, having a connector such as connector 100 or 200 from potential damage or corrosion that might otherwise occur when the contacts of the connector are exposed to a liquid, such as liquid 230. Embodiments of the disclosure can reliably detect the presence of a short circuit-causing liquid (e.g. sweat, pool water, tap water, sea water, rain, or a beverage) in an external connector of the electronic device and reduce or terminate the voltage supplied to the connector such that the voltage across the electrical contacts of the connector is reduced or dropped to zero in response to having detected the presence of the short-circuit or corrosion causing moisture. Embodiments of the disclosure can provide such protection while distinguishing instances when solids or liquids that are not likely to cause corrosion are present on one or more contacts instead of potentially harmful liquids.

In order to better appreciate and understand various embodiments of the disclosure, reference is made to FIG. 3, which is a simplified block diagram representing circuitry within a portable electronic device 300. Electronic device 300 can be, for example, a smart phone such as device 100 shown in FIG. 1. Embodiments of the disclosure can be useful for many other types of portable electronic devices, however, including laptop computers, tablet computers, and wearable devices, such as smart watches or headsets, among others that include an external connector built-in to the device but exposed to the ambient (and hence potential liquid intrusion). It is to be noted that while the various components discussed below with respect to FIG. 3 may be shown as separate blocks within the figure, embodiments of the disclosure do not require that each component be implemented as a separate circuit or chip. Indeed, the various components are illustrated and discussed as separate components in FIG. 3 for ease of discussion only. In some embodiments the functionality of two or more of the components can be combined together as a single chip or collection of shared components or circuitry and embodiments of the disclosure are not limited to the particular implementation described with respect to FIG. 3.

As shown in FIG. 3, portable electronic device 300 includes a connector 310, a multiplexor 320, and a liquid detection module (LDM) 330. Electronic device 300 can also include additional components 340 as appropriate to implement the functionality of device 300. In some embodiments additional components 340 can include a battery that provides power to device 300, a processor configured to control the overall operation of device 300, one or more computer-readable memories, a controller for a touch screen or other display device, data communication circuitry to implement one or more data communication protocols over connector 310, wireless communication circuitry to enable device 300 to wirelessly communicate with other electronic devices using known protocols, such as Bluetooth or WiFi, a global positioning system (GPS) receiver, and circuitry associated with sensors included within device 300 (e.g., an accelerometer, gryro, etc.) among other components. The nature and details of additional components 340 are not particularly important to the present disclosure and are thus not discussed in detail herein.

Connector 310 can be a computer peripheral serial bus connector, such as a Universal Serial Bus (USB) compliant connector, a Lightning connector developed by Apple Inc. or another connector that serves to pass both a power supply voltage as well as digital and/or analog control or communication signals to an external device. Connector 310 can include multiple contacts 315 located within a cavity (not shown in FIG. 3, but see cavity 210 in FIG. 2 as an example) into which a corresponding plug connector can be inserted during a mating operation. The multiple contacts 315 can include, for example, communication and control signal contacts, such as transmit and receive contacts or differential data contacts. Contacts 315 can also include a common ground contact that can be connected to ground and a power supply contact that can be connected to a power source. Embodiments of the disclosure are not limited to any particular example connector or pin configuration, however, and can be useful for any electronic device having a connector with two or more conductive paths. In some embodiments each of the two or more conductive paths can be connector contacts. For example, in some embodiments a first contact is employed as a sensing contact for the liquid intrusion test and a second contact provides a reference voltage. The reference voltage can be shared with power or ground. In other embodiments one of the conductive paths can be the housing or chassis of the connector and the second conductor (e.g., a connector contact) can be referenced to the housing or chassis. In various embodiments the sensing contact can be solely dedicated to the liquid detection function or can be dedicated to the liquid detection function for at least some portion of time and can be used for other functions (e.g., for control signals or data signals) at other times as described in more detail below.

Multiplexor 320 can be operatively coupled at an output to one or more of contacts 315 and at inputs to LDM 330 as well as to one or more communication interfaces or other circuitry represented by additional components 340. During normal operation, multiplexor 320 connects various ones of contacts 315 to communication circuitry within device 300 (represented in FIG. 3 by additional components 340) to enable device 300 to communicate over connector 310 with another electronic device. In some embodiments, connector 310 includes two pairs of data contacts and multiplexor 320 can switch each pair of data contacts between different communication circuitry providing flexibility for electronic device 300 to choose a communication protocol that is appropriate for a particular accessory that is connected to device 300 via connector 310. For example, in some embodiments device 300 can include separate sets of communication circuitry to implement a USB protocol (e.g., USB 2.0 or USB 3.0) and to implement a UART serial transmit and receive protocol and multiplexor 320 can connect each pair of data contacts to either USB or UART circuitry.

In some embodiments multiplexor 320 can also selectively route signals from LDM 330 onto one or more of the contacts 315 to conduct a liquid intrusion test as discussed below. In some embodiments the liquid detection testing signals are routed over a contact that is not currently being used for data signals, control signals or other purposes. In such embodiments, multiplexor 320 can decouple the pin from other circuitry within device 300 and connect the pin to LDM 330. In this manner, embodiments of the disclosure can conduct liquid detection tests without impairing or otherwise interrupting the normal communications that may be occurring over connector 310. In other embodiments, connector 310 can include one or more contacts 315 that are solely dedicated to the liquid detection operation in which case multiplexor 320 is not needed to couple and decouple circuitry to a particular contact for the liquid detection function. Additionally, in some embodiments the sensing conductor could be a dedicated part of the connector that does not form a contact, or it could be a power or ground pin that is temporarily decoupled from active circuits on both sides of the connector.

When a liquid intrudes within the cavity of connector 310 and comes into contact with one or more of contacts 315, energy can be stored at the contact by the double layer capacitance effect as discussed above. LDM 330 can generate and apply a time varying signal to a contact over a range of frequencies and can measure complex impedance at a contact in connector 310 to determine whether liquid intrusion has occurred on the contacts. In some embodiments, LDM 330 can apply a sinusoidal wave of voltage to a contact and measure the current that comes back. In other embodiments, LDM 330 can apply a sinusoidal wave of current to a contact and measure the voltage that comes back.

In the embodiment shown in FIG. 3, LDM 330 includes an analog front end (AFE) 332 and a digital processor 334. AFE 332 receives a pulse density modulation (PDM) signal 336 from digital processor 334. In other embodiments, a separate component, different from digital processor 334, may generate and send the PDM signal to AFE 332. PDM signal 336 is a binary signal that represents the frequency of a sinusoidal analog signal to be generated by AFE 332. In some embodiments AFE 332 can generate a sinusoidal waveform having a frequency between 10 Hz to 100 KHz as determined by the bit stream representing PDM signal 336. Embodiments of the disclosure are not limited to any particular range of frequencies, however, and other embodiments can generate a time varying signal at narrower or broader ranges as well as at ranges that start or end at lower or higher frequencies than 10 Hz and/or 100 KHz.

AFE 332 can also sample voltage or current measured at the contact being tested. The sampled data can then be sent over line(s) 338 to be analyzed by digital processor 334 to examine capacitive phase and magnitude shifts over the frequency of the signal to detect a potential double layer capacitor formed by the liquid. In some embodiments digital processor 334 is a digital signal processor (DSP) dedicated to the liquid detection process. In other embodiments, digital processor 334 can be included within an audio codec or similar component that electronic device 300 uses to code and decode digital data streams of audio for media playback and other purposes. In still other embodiments, digital processor 334 can be included within the main processing unit (represented by additional components 340) of electronic device 300 instead of a separate component.

Digital processor 334 can analyze the sampled data looking for signatures in phase and magnitude versus frequency that are indicative of a potentially harmful liquid as compared to a solid or a liquid that does not include any dissolved material and is thus likely to not be corrosive. In some embodiments, signal analyzer can employ a relatively straight forward decision tree in assessing whether a liquid or solid is present on the contacts. In other embodiments digital processor 334 can employ a more complex classifier using machine learning and pattern recognition techniques. The signatures can be based on data generated from previous measurements as discussed in more detail below. First, however, further details of one embodiment of AFE 332 are discussed below with respect to FIG. 4.

Figure 4:
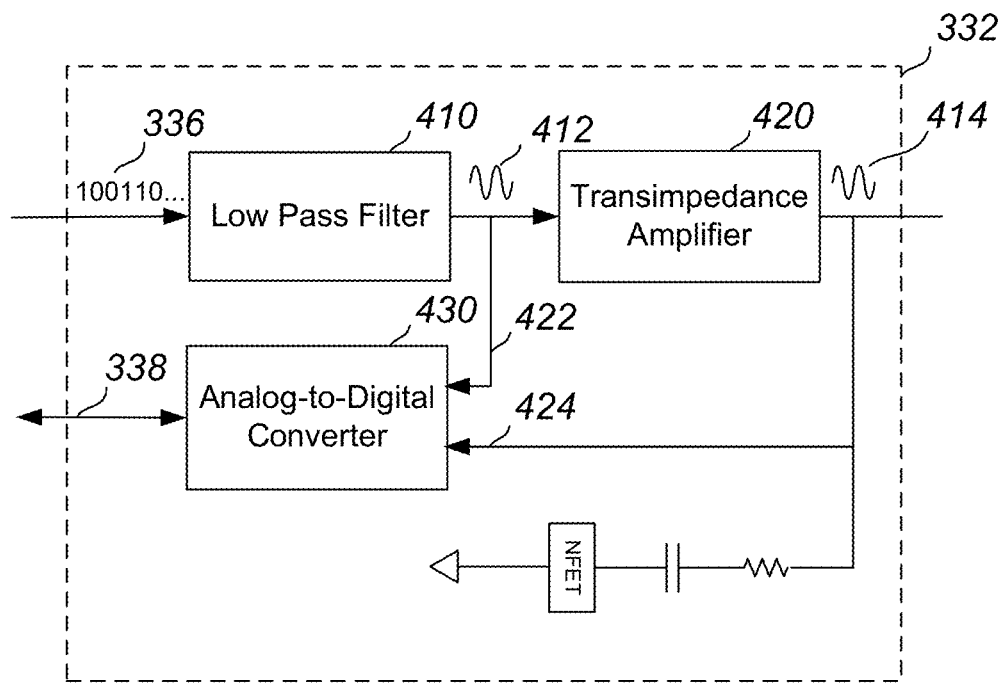
FIG. 4 is a simplified block diagram of analog front end 332 shown in FIG. 3 according to some embodiments of the disclosure.

As shown in FIG. 4, in some embodiments AFE 332 can include a low pass filter (LPF) 410, a transimpedance amplifier (TIA) 420 and a multi-channel analog-to-digital converter (ADC) 430, among other elements. Low pass filter 410 can be a single pole or double pole low pass filter. In some embodiments, LPF 410 receives PDM signal 336 and generates a current signal 412 in the form of a sine wave. TIA 420 is coupled to an output of LPF 410. TIA 420 can receive a current (sine wave 412) as input and convert the received current to a voltage (sine wave 414) as an output. TIA 420 thus drives both voltage and current lines 422, 424 to analog-to-digital converter 430 for the measurement of data that can be used to compute phase relationships.

Figure 5:
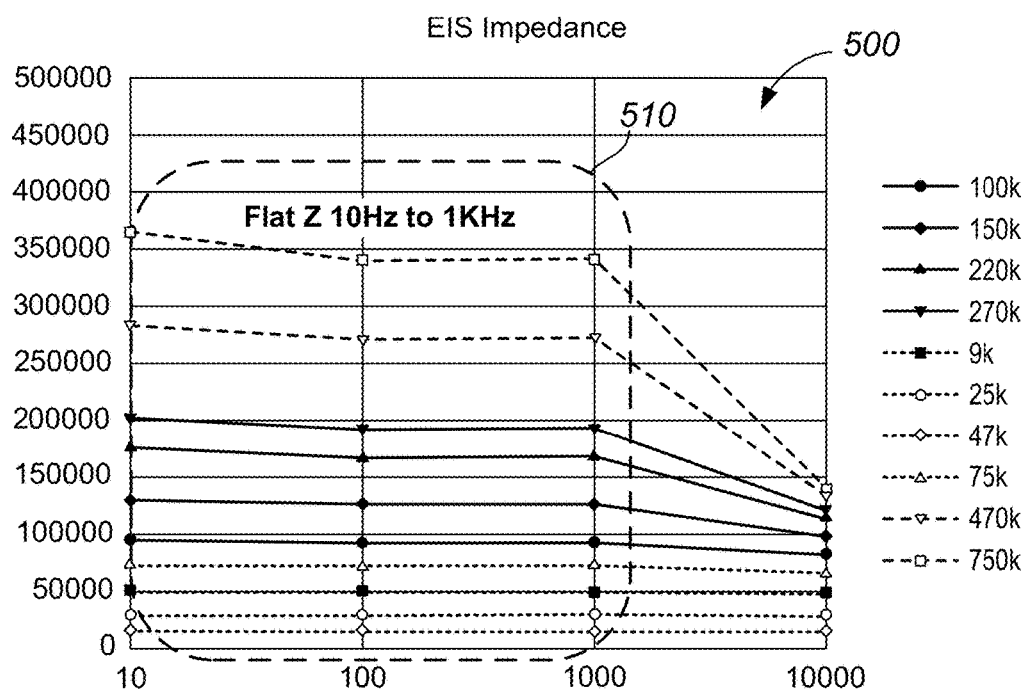
FIG. 5 is a graph depicting impedance measurements of different real resistors having different resistances measured at different frequencies.

To achieve accurate detection of a potentially harmful liquid on one or more contacts while minimizing false positive results, the inventors ran numerous experiments on both real resistors and various liquids to determine the characteristics of each at different frequencies using electrochemical impedance spectroscopy (EIS) measurements. The results of some of those experiments are set forth in FIGS. 5-8 and discussed below. FIG. 5 is a graph 500 depicting impedance measurements of 10 different real resistors having resistances ranging from 9,000 ohms to 750,000 ohms when a voltage sinewave was applied to each resistor at frequencies of 10 Hz, 100 Hz, 1,000 Hz and 10,000 Hz. As shown in area 510 of graph 500, impedance for all the resistors is generally flat in the 10 Hz to 1,000 Hz range.

Figure 6:
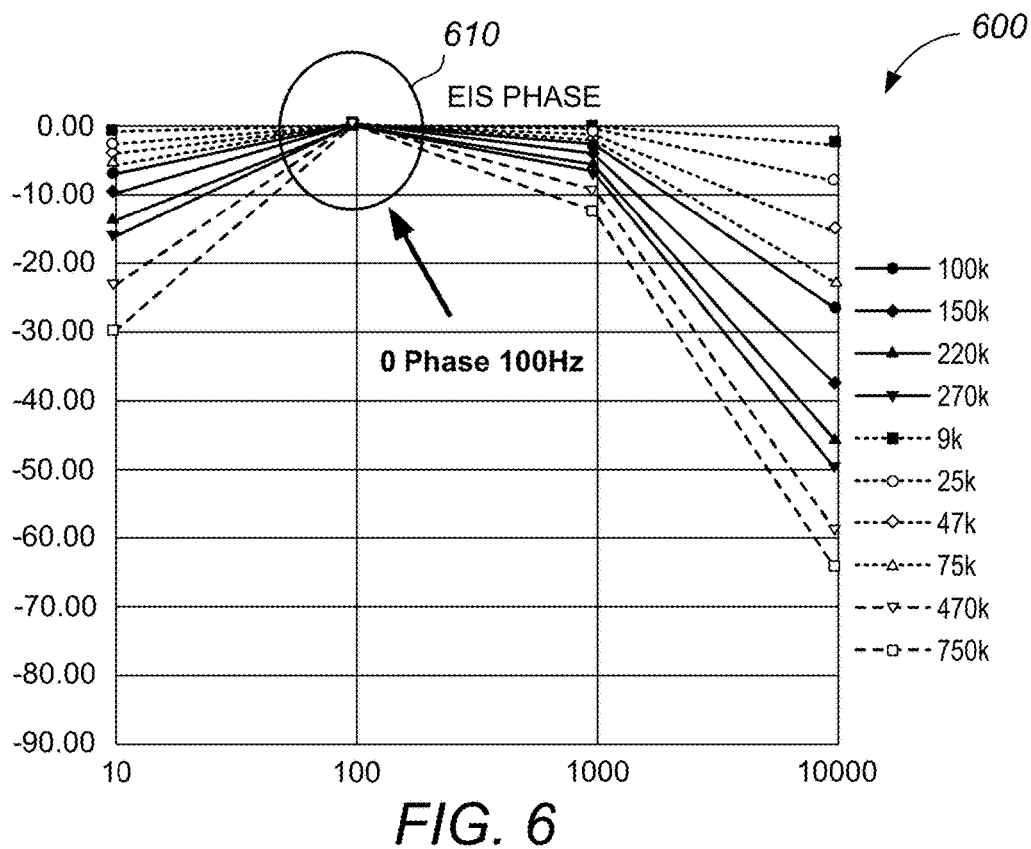
FIG. 6 is a graph illustrating the phase change of the resistors measured in FIG. 5 at different frequencies.

FIG. 6 is a graph 600 illustrating the phase change of the same resistors having resistances ranging from 9,000 ohms to 750,000 ohms as discussed with respect to FIG. 5. Graph 600 plots the phase change measured for each resistor at frequencies of 10 Hz, 100 Hz, 1,000 Hz and 10,000 Hz, respectively. As shown in area 610 in graph 600, none of the resistors exhibit any phase shift at 100 Hz. Said differently, all the resistors exhibit an essentially 0 degree phase shift at 100 Hz. Thus, FIGS. 5 and 6 represent characteristics that would be expected if a solid object or material (e.g., dirt, dust or other gunk) is on a contact being measured, such as one of contacts 315 in connector 310 discussed above with respect to FIG. 3.

Figure 7:
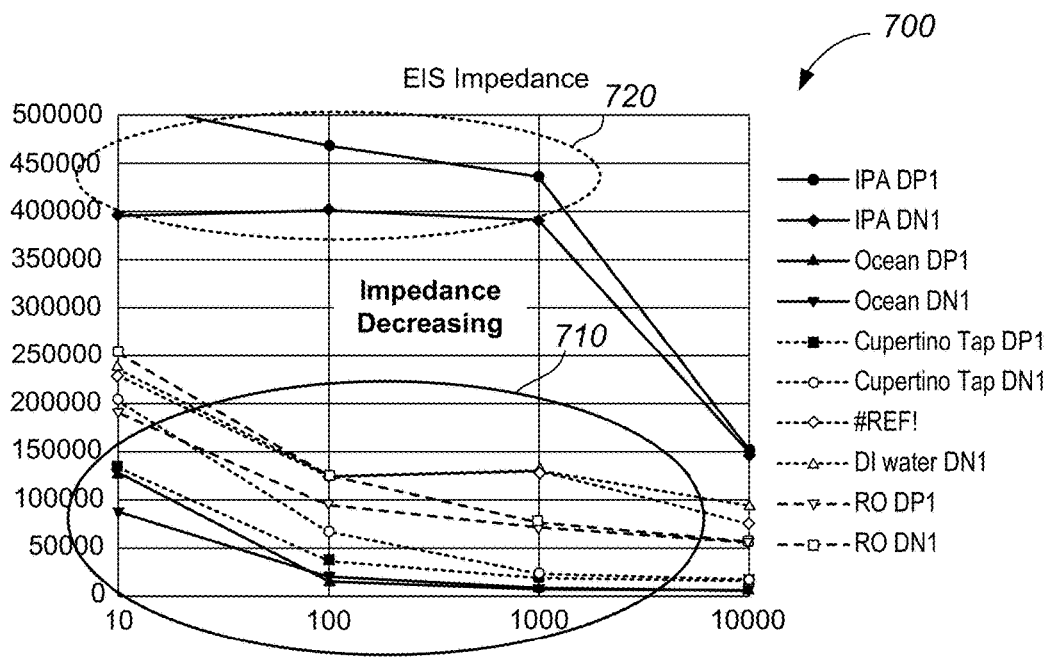
FIG. 7 is a graph depicting impedance measurements of different liquids measured at different frequencies.

When a liquid is present on a connector's contacts, the impedance and frequency shift characteristics over different frequencies are quite different from those shown in FIGS. 5 and 6 due to the double layer capacitance effect discussed above. FIG. 7 is a graph 700 depicting impedance measurements of 10 different types of liquids including various samples of tap water, ocean water, deionized water and isopropyl alcohol (IPA). As was done in FIG. 5, the measurements were taken when a voltage sinewave was applied to each liquid at different at frequencies of 10 Hz, 100 Hz, 1,000 Hz and 10,000 Hz. Graph 700 indicates that impedance for most of the liquid samples (samples 710) exhibits a decreasing impedance in the 10 Hz to 1,000 Hz range as compared to the flat impedance exhibited by the solids measured in FIG. 5. There are two outlying data sets in FIG. 7 (samples 720) in which the impedance characteristics of those liquid samples between 10-1,000 Hz is similar to the characteristics of a real resistor. The two samples 720 are both, however, clean IPA without dissolved materials that would cause corrosion. In most instances charging an electronic device, such as device 300 when the clean IPA from samples 720 is present on one or more contacts of the device would not promote corrosion on the contacts and would not present a problem. Thus, charging the electronic device under such circumstances (with clean IPA liquid on one or more of the device contacts) can be acceptable.

Figure 8:
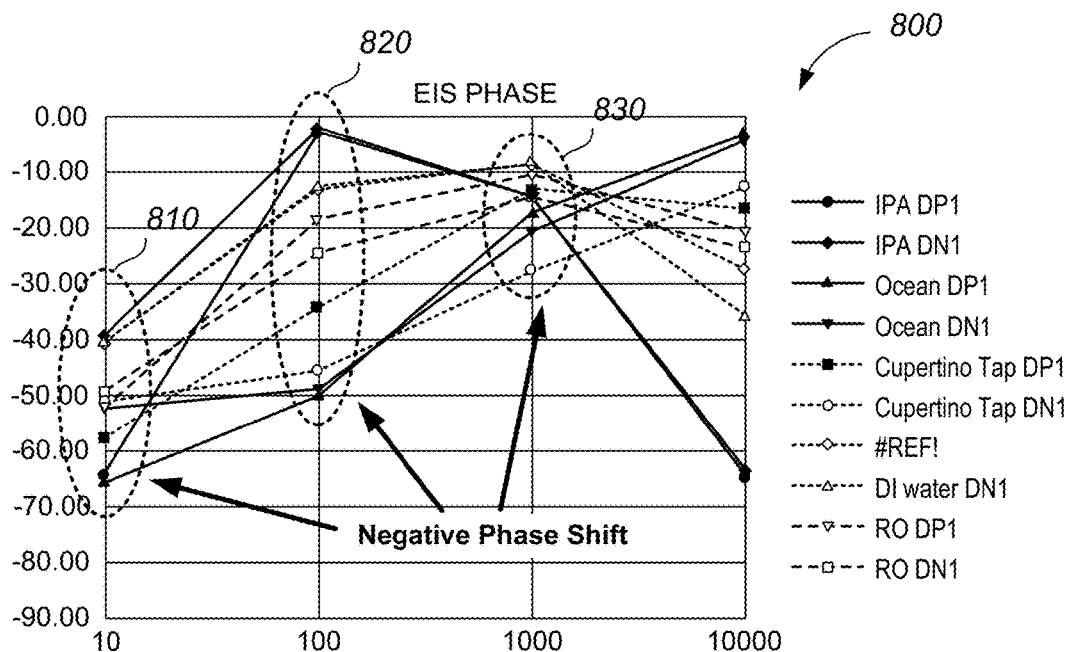
FIG. 8 is a graph illustrating the phase change of the resistors measured in FIG. 7 at different frequencies.

FIG. 8 is a graph 800 illustrating the phase change of the same liquids discussed with respect to FIG. 7 at frequencies of 10 Hz, 100 Hz, 1,000 Hz and 10,000 Hz. As shown in graph 800 by data set 810, all of the liquids measured exhibit a significant negative phase shift (greater than −30 degrees) at 10 Hz. Additionally, as shown by data set 820, all of the liquids except the two IPA samples exhibit a negative phase shift of at least −10 degrees) at 100 Hz, and as shown by data set 830, all of the liquids exhibit a negative phase shift of about −10 degrees or more at 1,000 Hz.

Figure 9A:
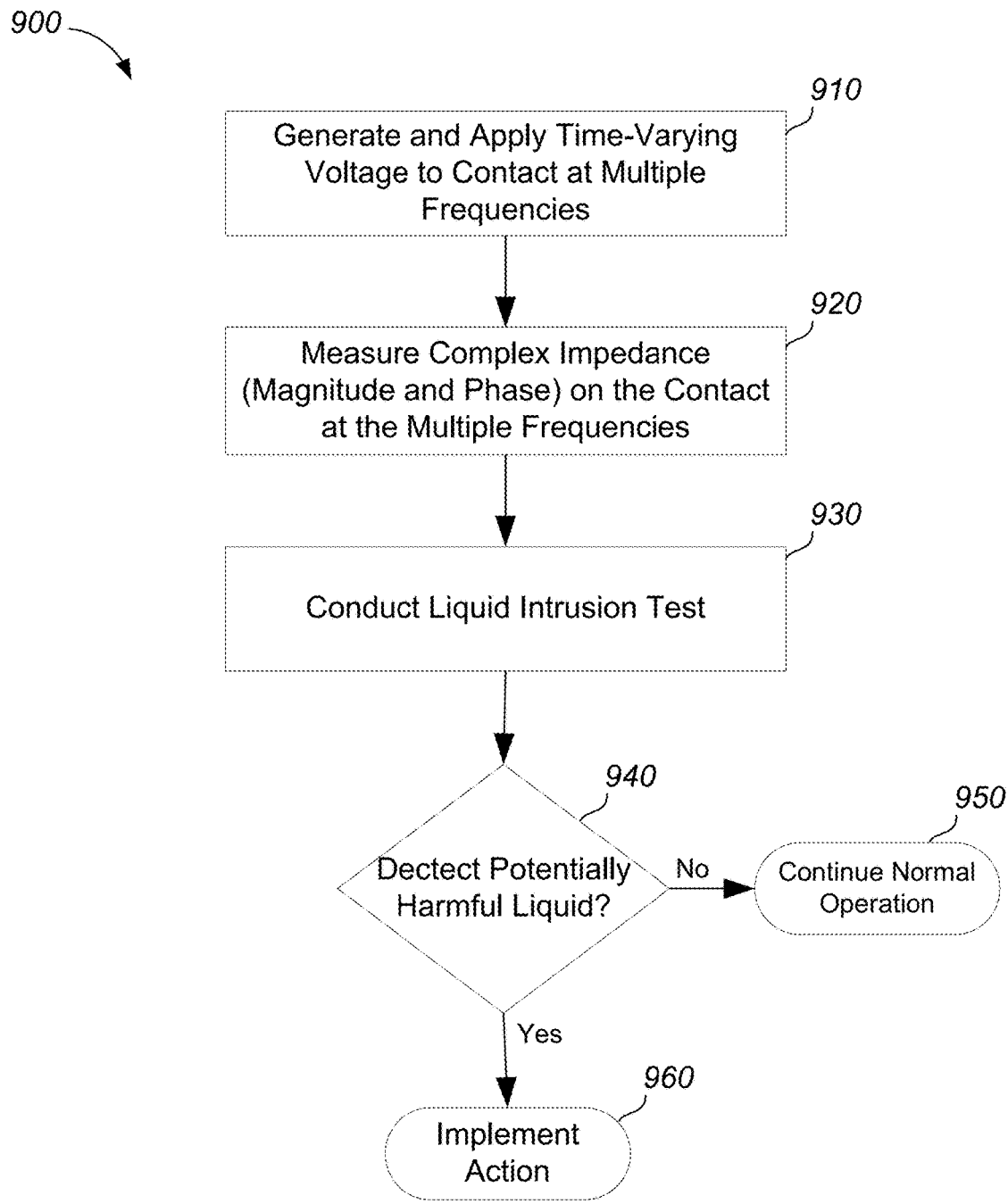
FIG. 9A is a flowchart illustrating the steps associated with a process for detecting liquid on a contact according to some embodiments of the disclosure.
Figure 9B:
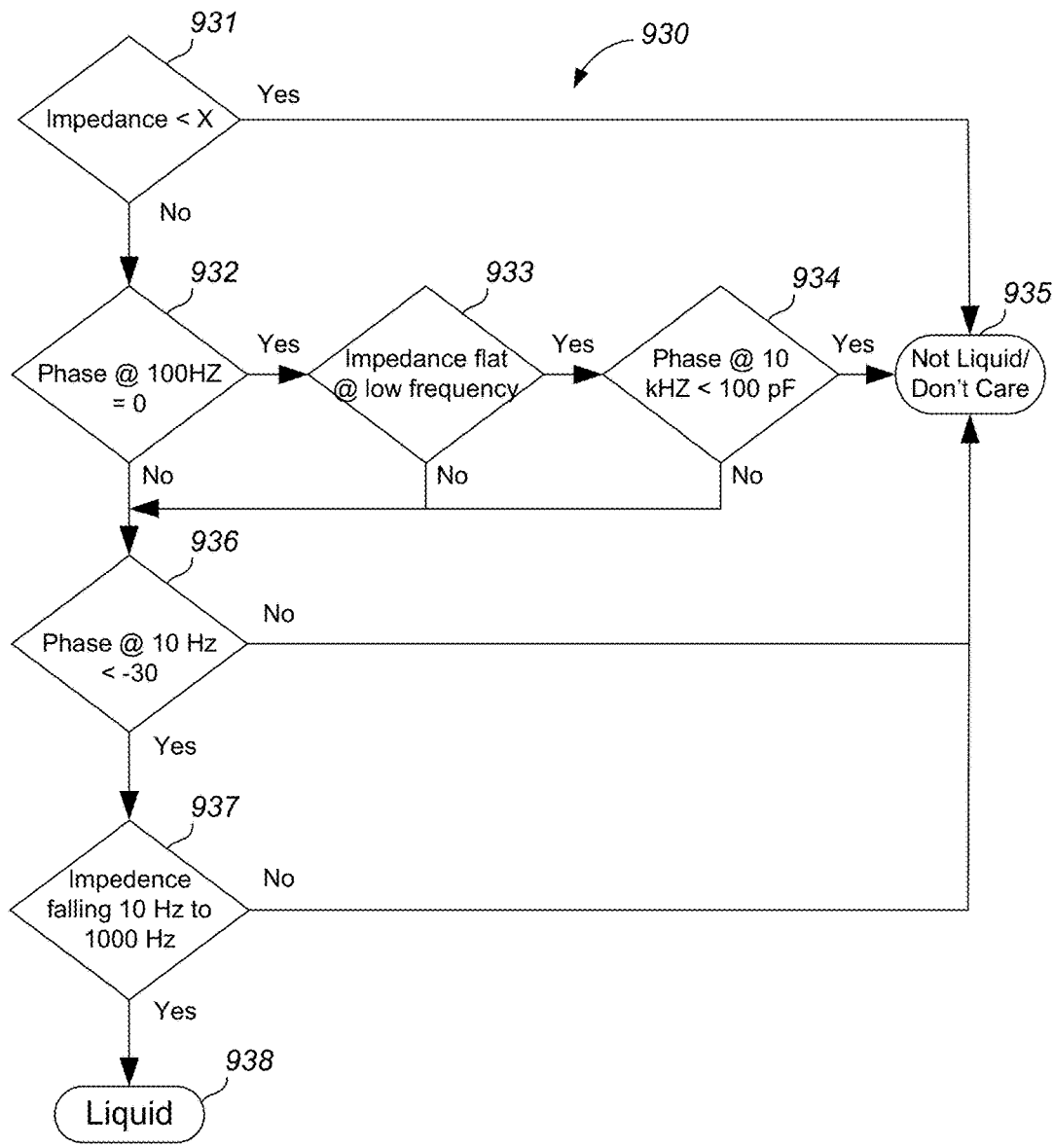
FIG. 9B is a flowchart illustrating a multi-step liquid intrusion test according to some embodiments of the disclosure.

After thoroughly reviewing and characterizing the measurements on both real resistor and various liquids from FIGS. 5-8 and other measurements, the inventors developed a multi-step test set forth in the flowchart of FIG. 9B that can be used to determine whether or not a potentially harmful liquid is present on a contact, such as one or more of contacts 315. The test in FIG. 9B can be conducted as part of an overall liquid detection process 900 set forth in the flowchart of FIG. 9A. As shown in FIG. 9A, liquid detection process 900 generates and applies a voltage signal to one or more contacts being tested in the manner described above at varying frequencies (step 910). In some embodiments, the voltage signal is applied as a sine wave at frequencies of 10 Hz, 100 Hz, 1,000 Hz and 10,000 Hz. As the voltage signal is applied to the contact, measurements are taken on both the phase and the magnitude of the voltage signal at each of the different frequencies at which it is applied (step 920). The measurements can then be compared to previously measured data of phase and magnitude versus frequency to determine whether or not potentially harmful liquid is present on the contact being tested (steps 930, 940). If no liquid is detected, electronic device 300 can continue its normal operation (step 950). If liquid is detected, electronic device can implement an appropriate action (step 960) as described below. The sequence of steps 910-940 can all occur in a relatively short time window and may be repeated periodically. If the liquid detection process is employed on a contact that may be used for another purpose, in step 910 multiplexor 320 decouples the contact from other circuitry within the electronic device and connects the contact to LDM 330. Once liquid detection method 900 is completed, multiplexor 920 can then decouple the contact from LDM 330 and reconnect the contact to the other circuitry.

In some embodiments the liquid intrusion test of step 930 is a multi-step test in which impedance and phase values measured during step 920 are compared to specific impedance and phase values from previously measured data sets the represent signatures of phase and magnitude versus frequency for known resistors having different resistance levels and different, known liquids. It is to be understood that test 930 set forth in FIG. 9B is just one example of a test that can be used to determine whether or not a potentially harmful liquid is present on an electrical contact. Embodiments of the disclosure are not limited to any particular test and are not limited to using the specific impedance or frequency values employed in the test. In other embodiments other tests can be employed to identify signatures in phase and magnitude versus frequency that are indicative of a potentially harmful liquid and to distinguish such signatures from signatures of a solid or a liquid that does not include any dissolved material and is thus likely to not be corrosive.

In some embodiments of the disclosure, multi-step test 930 can be implemented by digital processor 334 and associated circuitry shown in FIG. 3 and can be used by an electronic device, such as electronic device 300, to reliably determine if a potentially harmful liquid is present on one or more of contacts 315 while minimizing the number of false positives that may occur in such testing. As shown in FIG. 9B, in a first step of test 930 a determination is made as to whether the impedance measured on a contact being tested is greater than a predetermined value (step 931). In some embodiments the predetermined value is 300K ohms. In other embodiments other high resistance values can be used. If the resistance is above the predetermined value, test 900 can conclude that a potentially harmful liquid is not present on the contact (step 935) since, as evident from a FIGS. 5 and 7, the samples of potentially harmful liquids all have a resistance below 300K ohms.

If the resistance is less than the predetermined value, test 930 then checks the phase of the signal at 100 Hz (step 932). If the phase at 100 Hz (or a value close to 100 Hz) is zero or within a predetermined range of zero (e.g., ±5 degrees or ±2 degrees) it is likely that any material on the contact being tested is either not a liquid or a liquid that is not likely to cause corrosion as shown in FIGS. 6 and 8. In some embodiments, however, even when the phase at 100 Hz is zero, additional testing can be performed to further determine whether a liquid is present on the contacts. For example, as shown in FIG. 9B, a determination can be made as to whether or not the impedance at the contact is flat within a predetermined relatively low frequency range (step 933). In some embodiments, if step 933 determines that impedance is flat in the range of 10 Hz to 1,000 Hz range it is likely that any material on the contact being tested is either not a liquid or a liquid that is not likely to cause corrosion. Impedance can be determined to be flat if there is either no change in the impedance value in the tested range or if the amount of change is within a predetermined variance level (e.g., the impedance does not vary more than 5 percent or by more than 2 percent within the tested range).

If the impedance is determined to be flat in step 933, some embodiments can perform an additional test by determining if the capacitance at a particular frequency is less than a predetermined amount that represents the maximum stray capacitance in the measured circuit (step 934). As an example, in some embodiments step 934 determines the capacitance on the measured contact at 10 kHz and assumes that anything less than 100 pF indicates the contact is dry. To determine the capacitance embodiments of the disclosure can measure the magnitude and phase of the impedance between the signal and the reference and derive capacitance from the vector of the magnitude and phase of the measurement according to the following formula:

$$C=1/(2\times\pi\times\text{frequency}\times\text{imaginary impedance}) \quad (1)$$

where the magnitude times the cosine of the phase equals the real part of the impedance, and where the magnitude times the sine of the phase equals the imaginary part of the impedance.

If each of steps 931, 932, 933 and 934 generate positive results, it is likely that any material on the contact being tested is not a liquid (step 935). If, instead, step 932 determines that the phase at 100 Hz is not zero, step 933 determines that impedance is not flat in the predetermined range, or step 934 generates negative results (i.e., the capacitance at a specified predetermined frequency is greater than the predetermined amount, e.g., 100 pF), test 930 next checks whether the phase at a low frequency (e.g., 10 Hz) is less than a predetermined negative value (step 936). In some embodiments, step 936 checks to see if the phase at 10 Hz is less than −30 degrees. If the phase is not less than −30 degrees, a comparison of FIGS. 6 to 8 indicates that it is likely that any material on the contact being tested is not a liquid (step 935).

If step 936 indicates that the phase at 10 Hz is less than the predetermined value, test 900 can proceed to determine whether the impedance at the contact is falling between 10 Hz and 1,000 Hz as shown, for example, in FIG. 7 as data set 710. If the impedance is not falling within the tested range, it is likely that any material on the contact being tested is not a liquid (step 935) as evident from the data points in graph 500 of FIG. 5.

If the impedance is falling in step 937, having met the threshold for each of the previous steps 931, 932 and 933, test 930 can determine that the material on the contact(s) being tested is likely to be a potentially harmful liquid and take appropriate action (FIG. 9A, step 960) including, for example, terminating power to connector 310 or reducing the voltage delivered to individual contacts 315 in order to reduce corrosion build-up. As mentioned above, test 930 is just one example of a test that can be employed to detect liquid intrusion. Embodiments of the disclosure are not limited to any particular test and other embodiments may include fewer or more decision branches than what is shown in FIG. 9B and/or may rely on different values of either or both impedance and phase shift in each decision branch. In general, embodiments of the disclosure look for signatures in phase and magnitude versus frequency that are indicative of a potentially harmful liquid as compared to a solid or a liquid that does not include any dissolved material and is thus likely to not be corrosive. The signatures can be based on measured values from previously run tests and can be detected by decision-tree logic, such as set forth in FIG. 9B, by using more complicated machine-learning techniques or by using other pattern recognition techniques.

Figures 10, 11:
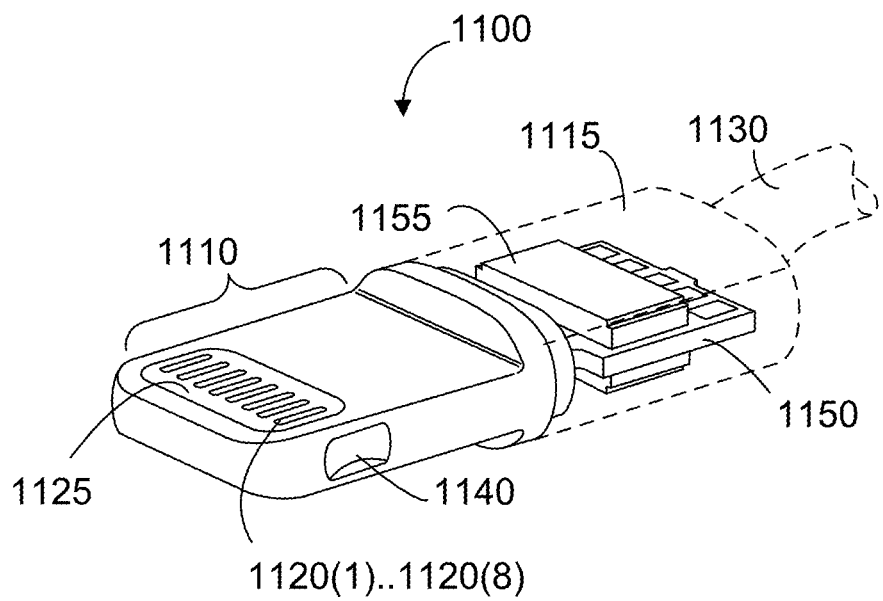
FIG. 10 is a table of properties that can be used in a test for liquid intrusion according to some embodiments of the disclosure.
FIG. 11 shows a perspective view of a plug connector that can be mated with receptacle connector 200 shown in FIG. 2 according to some embodiments of the disclosure.

When the decision logic is based on the test results from FIGS. 5-8, the table set forth in FIG. 10 lists some of the various tests that can be conducted as part of a test to determine whether or not a potentially harmful liquid is present on connector contacts. These variables can be worked into a decision tree such as that shown in FIG. 9B or a process that uses a different sequence of decisions. As shown in FIG. 10, it is likely that the tested contact is dry (or is in contact with a liquid that does not cause corrosion) if the impedance is greater than 300K ohms, the impedance is flat from 10 Hz to 1,000 Hz, the phase is zero or essentially zero at 100 Hz and/or the phase at 10,000 Hz matches characteristics less than 100 pF. It is likely that a potentially harmful and corrosive liquid has intruded onto the contacts of an electronic device, however, if the impedance is falling from 10 Hz to 1,000 Hz, the phase at 10 Hz is less than negative 30 and/or the phase at 10 Hz and 1,000 Hz is less than negative 10.

Once electronic device 300 determines that a potentially harmful liquid is present on its contacts, a variety of actions can be undertaken (FIG. 9A, step 960). For example, in various embodiments, device 300 can do one or more of the following: (1) reduce the voltage on the contacts in order to reduce any corrosion that might otherwise occur; (2) terminate the voltage on the contacts by reducing the voltage to zero (terminating the voltage will stop whatever functionality, e.g., charging device 300, was going to be carried out over the contacts); and (3) alert a user of the device that liquid has been detected on the contacts. The alert can be in the form of a message displayed on the device screen, an indicator light, a beep or any other suitable means.

In some embodiments, electronic device 300 can delay implementing the function (e.g., by software executing on the device's main processor) for a predetermined amount of time after detecting liquid intrusion. For example, if a charging cable is mated with electronic device 300 and device 300 determines that liquid is present on contacts 315, device 300 may delay the initiating of the charging operation for an hour or some other predetermined amount of time that is believed to be sufficient to allow the liquid to dry before initiating charging. In other embodiments, after detecting liquid on the contacts device 300 can implement a timer to rerun test 900 every X minutes (e.g., 5, 10 or 15 minutes) until liquid is no longer detected. Thus, for example, if it takes half an hour for the liquid to fully dry such that test 930 can be passed, device may run test 930 at 0 minutes, 10 minutes, and 20 minutes with the test failing on each occasion. When test 930 then passes on the fourth attempt, charging can be initiated.

In other embodiments, electronic device 300 can initiate charging even when liquid is detected on contacts 315 but then run test 930 again every Y minutes (e.g., 5, 10 or 15 minutes) to determine if liquid is still present. If a small amount of liquid was present when charging was initiated, the charging process may result in a small amount of corrosion that is not particularly detrimental to the contacts. Gases can be generated during the corrosion forming process that consume the liquid. Thus, if a fixed amount of liquid is present within the connector, the corrosion forming process is self-limiting and test 930 can be passed when subsequently run a second, third or some future iteration. If after a predetermined number of attempts test 930 is still not passed, electronic device 300 can terminate the charging process. This may occur, for example, if device 300 is exposed to an ongoing large source of liquid (e.g., a puddle or a user continuously sweating).

Additionally, in some embodiments, portable electronic device 300 can include a context awareness module (not shown) that can be, for example, a software program that collects various data (including output from one or more sensors included within device 300) within electronic device 300 and analyzes the collected data to form various conclusions on context awareness (including location awareness). The context awareness data may include context types such as the location of device 300, the identity and role of a user of device 300, the activity in which the user is engaged and the time of day. The context awareness data can be used to determine whether or not to initiate test 930. For example, in some embodiments, test 900 might only be initiated if the context awareness module determines that there is a higher than a predetermined percent chance that liquid may have intruded into the connector cavity.

Reference is now made to FIG. 11, which is a simplified perspective view of a plug connector 1100 that can be mated with connector 200. Plug connector 1100 includes an insertion end 1110 that extends longitudinally away from a body 1115 in a direction parallel to the length of the connector. Eight external contacts 1120(1) . . . 1120(8) are formed at an exterior surface of the insertion end and spaced apart along a single row in a contact region 1125. Contacts 1120(1) . . . 1120(8) can be used to carry a wide variety of signals including data signals and power and ground. In some embodiments plug connector 1100 is a reversible connector having a second set of eight contacts in a second contact region on the side opposite that shown in FIG. 11.

A cable 1130 can be attached to body 1115 at an end opposite of insertion end 1110. The insertion end 1110 is sized to be inserted into the cavity of receptacle connector 200 during a mating event. Connector 1100 also includes retention features 1140 on opposing sides of the connector (only one is visible in FIG. 11) formed as curved pockets in the sides of insertion end. Body 1115 is shown in transparent form (via dotted lines) so that certain components inside the body are visible including a printed circuit board (PCB) 1150 that extends into insertion end 1110. One or more integrated circuits (ICs), such as Application Specific Integrated Circuit (ASIC) chip 1155, can be operatively coupled to PCB 1150 to perform specific functions, such as authentication, identification, contact configuration and current or power regulation.

While certain embodiments have been described and shown in the accompanying drawings, it is to be understood that such embodiments are merely illustrative of and not restrictive on the broad invention, and that the invention is not limited to the specific constructions and arrangements shown and described, since various other modifications may occur to those of ordinary skill in the art. For example, while embodiments of the disclosure were primarily discussed with respect to detecting liquid on a receptacle connector, such as connector 100 or 200, embodiments of the disclosure can also be used to detect liquid on a plug connector, such as connector 1100 or other types of plug connectors. The description above is thus to be regarded as illustrative instead of limiting.

What is claimed is:

1. An electronic device comprising:
   a connector including a plurality of contacts;
   a liquid detection module, coupled to at least one contact in the plurality of contacts, the liquid detection module configured to: (i) generate and apply a time varying voltage or current to the at least one contact at a plurality of different frequencies; (ii) measure complex impedance including phase and magnitude at the at least one contact at each of the plurality of different frequencies; and (iii) determine whether liquid intrusion has occurred on the contacts based on previously measured signatures of phase and magnitude versus frequency.

2. The electronic device of claim 1 wherein the liquid detection module generates the time varying voltage or current as a sinewave from a pulse density modulation (PDM) signal.

3. The electronic device of claim 1 wherein the liquid detection module generates a time varying signal as a current sinewave from a pulse density modulation (PDM) signal and converts the current sinewave to a voltage sinewave that is applied to the at least one contact in the plurality of contacts.

4. The electronic device of claim 3 wherein the liquid detection module comprises a low pass filter that receives the PDM signal as input and outputs the current sinewave.

5. The electronic device of claim 4 wherein the liquid detection module further comprises a transimpedance amplifier that receives the current sinewave as input and generates the voltage sinewave.

6. The electronic device of claim 5 wherein the liquid detection module further comprises an analog-to-digital converter having a first input coupled to an output of the low pass filter and a second input coupled to an output of the transimpedance amplifier.

7. The electronic device of claim 1 further comprising communication circuitry that enables the electronic device to communicate with another electronic device over the at least one contact and a multiplexor is configured to switch the at least one contact between the communication circuitry and the liquid detection circuitry.

8. The electronic device of claim 1 wherein the liquid detection module comprises an audio codec and uses the audio codec to determine whether liquid intrusion has occurred on the contacts based on previously measured signatures of phase and magnitude versus frequency.

9. An electronic device comprising:
   a connector including a plurality of contacts;
   a liquid detection module, coupled to at least one contact in the plurality of contacts, the liquid detection module configured to: (i) generate and apply a time varying voltage or current to the at least one contact over a range of frequencies; (ii) measure complex impedance includ-ing phase and magnitude at the at least one contact and (iii) determine whether liquid intrusion has occurred on the contacts based on previously measured signatures of phase and magnitude versus frequency;
   wherein the liquid detection module employs a test that includes detecting whether the measured impedance on the at least one contact is greater than a predetermined amount and whether the measured phase on the at least one contact is essentially zero at a predetermined frequency to determine whether liquid intrusion has occurred on the contacts based on previously measured signatures of phase and magnitude versus frequency.

10. An electronic device comprising:
    a connector comprising a plurality of contacts including at least a voltage contact and a signal contact;
    signal generating circuitry configured to generate a control signal or data signal;

an analog-to-digital converter;

a digital processor configured to generate a pulse density modulation (PDM) signal and to receive complex impedance measurements of the at least one contact including phase and magnitude from the analog-to-digital converter, the digital processor being further configured to determine whether liquid intrusion has occurred on one or more of the contacts based on previously measured signatures of phase and magnitude versus frequency;

a low pass filter configured to receive the pulse density modulation (PDM) signal at an input and output a current sine wave at a frequency indicated by the PDM signal;

a transimpedance amplifier coupled at an input to receive the current sinewave from the low pass filter and output a voltage sine wave;

the analog-to-digital converter having a first input coupled to the output of the low pass filter and a second input coupled to the output of the transimpedance amplifier; and a multiplexor coupled to the signal generating circuitry, to the output of the transimpedance amplifier and to the signal contact, the multiplexor configured to switch the signal contact between the signal generating circuitry and the transimpedance amplifier.

11. The electronic device of claim 10 wherein the digital processor comprises an audio codec.

12. The electronic device of claim 11 wherein the digital processor generates a series of PDM signals to alter the frequency of the current sine wave generated by the low pass filter.

13. The electronic device of claim 11 wherein the digital processor is configured to employ a test that includes detecting whether the measured impedance on the at least one contact is greater than a predetermined value and whether the measured phase on the at least one contact is essentially zero at a predetermined frequency to determine whether liquid intrusion has occurred on the contacts.

14. The electronic device of claim 11 wherein the test employed by the digital signal processor concludes that liquid is not present on the at least one contact if the impedance on the at least one contact is greater than the predetermined value.

15. A method for detecting a liquid on a contact of a connector, the method comprising:
generating and apply a time varying voltage or current to the contact at a plurality of different frequencies;
measuring complex impedance including phase and magnitude at the contact at each of the plurality of different frequencies; and
determining whether liquid intrusion has occurred on the contacts based on previously measured signatures of phase and magnitude versus frequency.

16. The method of claim 15 wherein the step of generating and applying includes generating a current sine wave from a pulse density modulation (PDM) signal and converting the current sinewave to a voltage sinewave that is applied to the contact.

17. The method of claim 15 further comprising, when it is determined that a liquid is present on the contact, reducing the voltage on the contact.

18. The method of claim 15 further comprising, if it is determined that a liquid is present on the contact, terminating the voltage on the contact.

19. The method of claim 15 further comprising, if it is determined that a liquid is present on the contact, delaying initiation of a function until a predetermined amount of time has expired.

20. The method of claim 15 further comprising, prior to the generating and applying step, decoupling the contact from a first set of circuitry within an electronic device and coupling the contact to second set of circuitry to perform the generating and applying step.

* * * * *